(12) United States Patent
Publicover et al.

(10) Patent No.: US 9,405,365 B2
(45) Date of Patent: *Aug. 2, 2016

(54) SYSTEMS AND METHODS FOR IDENTIFYING GAZE TRACKING SCENE REFERENCE LOCATIONS

(71) Applicant: EYEFLUENCE, INC., Reno, NV (US)

(72) Inventors: Nelson G. Publicover, Reno, NV (US); William C. Torch, Reno, NV (US); Gholamreza Amayeh, Reno, NV (US); David Leblanc, Reno, NV (US)

(73) Assignee: EYEFLUENCE, INC., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/537,823

(22) Filed: Nov. 10, 2014

(65) Prior Publication Data
US 2015/0169050 A1 Jun. 18, 2015

Related U.S. Application Data

(63) Continuation of application No. 13/113,003, filed on May 20, 2011, now Pat. No. 8,885,877.

(51) Int. Cl.
| | |
|---|---|
| *G06K 9/00* | (2006.01) |
| *G06F 3/01* | (2006.01) |
| *A61B 3/113* | (2006.01) |
| *G02B 27/01* | (2006.01) |
| *G02B 27/00* | (2006.01) |
| *G06T 7/00* | (2006.01) |

(52) U.S. Cl.
CPC ............... *G06F 3/013* (2013.01); *A61B 3/113* (2013.01); *G02B 27/0093* (2013.01); *G02B 27/017* (2013.01); *G06K 9/00604* (2013.01); *G06T 7/0044* (2013.01); *G02B 2027/014* (2013.01); *G02B 2027/0138* (2013.01); *G02B 2027/0178* (2013.01); *G02B 2027/0187* (2013.01); *G06T 2207/10016* (2013.01); *G06T 2207/10024* (2013.01); *G06T 2207/30204* (2013.01)

(58) Field of Classification Search
None
See application file for complete search history.

(56) References Cited

U.S. PATENT DOCUMENTS

| | | | | |
|---|---|---|---|---|
| 5,739,912 | A * | 4/1998 | Ishii | 356/602 |
| 6,184,863 | B1 * | 2/2001 | Sibert et al. | 345/156 |
| 6,191,819 | B1 * | 2/2001 | Nakano | 348/333.03 |
| 6,307,589 | B1 * | 10/2001 | Maquire, Jr. | 348/333.03 |
| 6,373,961 | B1 * | 4/2002 | Richardson et al. | 382/103 |
| 6,608,615 | B1 * | 8/2003 | Martins | 345/156 |

(Continued)

*Primary Examiner* — Shervin Nakhjavan
(74) *Attorney, Agent, or Firm* — William A. English; Vista IP Law Group LLP

(57) ABSTRACT

A system is provided for identifying reference locations within the environment of a device wearer. The system includes a scene camera mounted on eyewear or headwear coupled to a processing unit. The system may recognize objects with known geometries that occur naturally within the wearer's environment or objects that have been intentionally placed at known locations within the wearer's environment. One or more light sources may be mounted on the headwear that illuminate reflective surfaces at selected times and wavelengths to help identify scene reference locations and glints projected from known locations onto the surface of the eye. The processing unit may control light sources to adjust illumination levels in order to help identify reference locations within the environment and corresponding glints on the surface of the eye. Objects may be identified substantially continuously within video images from scene cameras to provide a continuous data stream of reference locations.

19 Claims, 6 Drawing Sheets

(56) References Cited

U.S. PATENT DOCUMENTS

| | | | |
|---|---|---|---|
| 6,657,673 B2* | 12/2003 | Ishikawa | 348/376 |
| 7,206,022 B2* | 4/2007 | Miller et al. | 348/333.03 |
| 7,259,785 B2* | 8/2007 | Stavely et al. | 348/231.3 |
| 7,418,116 B2* | 8/2008 | Fedorovskaya et al. | 382/118 |
| 7,736,000 B2* | 6/2010 | Enriquez et al. | 351/210 |
| 8,401,248 B1* | 3/2013 | Moon et al. | 382/118 |
| 2001/0010514 A1* | 8/2001 | Ishino | 345/158 |
| 2003/0169233 A1* | 9/2003 | Hansen | 345/158 |
| 2005/0227217 A1* | 10/2005 | Wilson | 434/337 |
| 2006/0092307 A1* | 5/2006 | Mori et al. | 348/333.01 |
| 2006/0209013 A1* | 9/2006 | Fengels | 345/156 |
| 2006/0210117 A1* | 9/2006 | Chang et al. | 382/113 |
| 2011/0043644 A1* | 2/2011 | Munger et al. | 348/207.1 |
| 2011/0052009 A1* | 3/2011 | Berkovich et al. | 382/106 |
| 2012/0154557 A1* | 6/2012 | Perez et al. | 348/53 |
| 2012/0290401 A1* | 11/2012 | Neven | 705/14.68 |

* cited by examiner

SYSTEMS AND METHODS FOR IDENTIFYING GAZE TRACKING SCENE REFERENCE LOCATIONS

RELATED APPLICATION DATA

The present application is a continuation of application Ser. No. 13/113,003, filed May 20, 2011, issuing as U.S. Pat. No. 8,885,877, the entire disclosure of which is expressly incorporated by reference herein.

STATEMENT REGARDING FEDERALLY SPONSORED RESEARCH AND DEVELOPMENT

The U.S. Government may have a paid-up license in this invention and the right in limited circumstances to require the patent owner to license others on reasonable terms as provided for by the terms of Department of Defense (US Army) Contract No. W81XWH-05-C-0045, U.S. Department of Defense Congressional Research Initiatives No. W81XWH-06-2-0037 and W81XWH-09-2-0141, and U.S. Department of Transportation Congressional Research Initiative Agreement Award No. DTNH 22-05-H-01424.

FIELD OF THE INVENTION

The present invention relates to apparatus, systems, and methods for unobtrusively identifying reference locations within the environment of a device wearer for gaze tracking and other applications.

BACKGROUND OF THE INVENTION

The apparatus, systems, and methods herein utilize machine vision techniques to track locations and objects being viewed by an observer. Gaze tracking algorithms can be considered as requiring two continuous data streams in order to produce accurate tracking results: 1) eye tracking methods to detect the edges of pupils or other identifiable reference points within the eye to compute pivot angles and viewing directions of the eye, and 2) head tracking methods to locate the position and orientation of the head within our three-dimensional world.

Generally, head tracking can involve identifying the location of a rigid object affixed to the head (as opposed to the head itself). In this case, headwear or eyewear that is affixed to the head has known geometries and displacements relative to the head or reference points on the head that can be computed. More specifically, for accurate gaze tracking, a head tracking apparatus should have a known displacement from the pivot point of one or both eyeballs of the observer. Furthermore, for most applications, gaze tracking locations are determined relative to reference locations or objects within the environment of a device wearer, such as the corners of a display monitor, a mobile computing device, a switch, a light source, a window, and the like.

Applications that involve machine vision are becoming increasingly common-place. In part, this has arisen as a result of technological advances in the electronics and software development industries, and decreases in the cost of cameras, information processing units, and other electronics components. Gaze tracking, in particular, is increasingly being used in a number of diagnostic, human performance, and control applications. A small number of examples include monitoring the degree of fatigue of an individual, assessing driver or pilot awareness, assessing the effects of drugs or alcohol, diagnosing post-traumatic stress disorder, tracking human performance with age, determining the effectiveness of training or exercise, assessing the effectiveness of advertising and web-page design by measuring ocular dwell times, magnifying or changing the brightness of specific objects or images (including words) under observation, controlling various aspects of games, acquiring foundational clinical data to assess neurological or cognitive disorders, diagnosing and monitoring degenerative eye conditions, and allowing individuals with limited or no mobility below the neck to communicate by controlling a computer cursor using one or more eyes and eyelids. Sectors and industries that utilize gaze tracking include military, medicine, security, human performance, sports medicine, rehabilitation engineering, police, research laboratories, and toys.

In almost all cases, an increase in the accuracy of gaze tracking leads to an increase in the performance and convenience of most applications. For example, with increased accuracy, ocular dwell times to quantify fixation times on smaller objects or components of objects can be more accurately measured. Gaze tracking can be more effectively employed with portable devices that utilize smaller screens including mobile phones and hand-held displays. When gaze tracking is used to control a cursor involving selection from a number of virtual objects or icons within a screen, an increased number of selectable objects can be displayed simultaneously because of the ability to use smaller virtual objects or icons. An increased number of objects within each level of a selection process has a dramatic effect on the efficiency (i.e., reduced number of selection levels and/or reduced time) that a virtual object and associated action can be chosen. Similarly, enlarging or increasing the brightness levels of objects and words under observation can significantly increase recognition and reading rates of individuals who are visually impaired.

Many gaze tracking systems use cameras and eye illuminators that are located at a considerable distance (e.g., greater than ten centimeters (10 cm)) from an eye. As the distance away from the eyes is increased, an eye tracking apparatus generally becomes less obtrusive; however, it becomes increasingly difficult to accurately measure the location of an eye because of the need for higher spatial resolution by cameras and because wide-ranging head movement can cause the complete loss of the ability to track an eye. Many gaze tracking systems also use bright (visible or invisible) "point" sources of light located some distance from the head to produce glints or bright spots on the surface of the eye. These glints can be used to generate reference vectors from the location of the glint on the surface of the eye to known locations in the environment (i.e., the light sources). Here again, wide-ranging movements of the head can cause loss of the ability to track glints and/or the ability to associate a glint with a particular light source.

With the advent of modern-day microelectronics and micro-optics, it is possible to unobtrusively mount the components for gaze tracking on eyewear (e.g., eyeglasses frames) or headwear (e.g., helmet, mask, goggles, virtual reality display) including those devices disclosed in U.S. Pat. No. 6,163,281, 6,542,081, or 7,488,294, 7,515,054, the entire disclosures of which are expressly incorporated by reference herein. Using high-precision micro-optics within the eyewear or headwear, it is possible to more clearly resolve structures and reflections within the eye and nearby regions, as well as the scene viewed by the device wearer. The use of low-power, miniature cameras and electronics permits a head-mounted system to optionally be non-tethered through the use of a battery power source. Furthermore, recent advances in wireless telecommunications allow gaze tracking results to be transmitted in real-time to other computing, data storage, or control devices. As a result of these technological advances in a number of fields, an eyewear- or headwear-based gaze tracking system can be unobtrusive, light-weight, portable and convenient to use.

SUMMARY OF THE INVENTION

Gaze tracking involves substantially continuously identifying the locations and/or objects being viewed by an observer. Accurate gaze tracking results from a combination of eye tracking and head tracking relative to identified reference locations within our 3-dimensional world. The apparatus, systems, and methods herein utilize an unobtrusive scene camera mounted on eyewear or headwear to identify naturally occurring or intentionally placed reference locations in the environment of the wearer.

More specifically, the apparatus, systems, and methods herein may facilitate unobtrusively identifying reference locations within the environment of the device wearer for gaze tracking and other applications. In one embodiment, systems and methods for determining scene reference locations may include a device configured to be worn on a person's head; a scene camera connected to the device and positioned for capturing images of the environment of the wearer; a scene processor operatively connected to the scene camera for determining scene reference locations within the scene camera images; an eye-tracking camera connected to the device and positioned for capturing eye-tracking locations of at least one of the wearer's eyes; and a processor that uses scene reference locations and eye-tracking locations to determine locations being viewed by the wearer.

Reference locations within a scene may be identified using one or more characteristics of objects including an object's shape size, or color. The spatial relation among various geometric shapes such as those found on one- and two-dimensional bar codes, QR (i.e., quick response) codes, matrix (i.e. two-dimensional) codes, and the like may also be used for location identification and orientation. Objects that define reference locations may be intentionally placed within the wearer's environment; such as colored pieces of paper or plastic, pigmented (e.g., paint or ink) spots, colored (or black and white) regions within a display screen, light sources, and/or reflective surfaces. Alternatively, reference locations may be extracted using object recognition techniques from an unaltered wearer's environment such as the corners of a display screen, the corners of a mobile phone or reader (e.g., iPad® or Kindle® device), the central location of a larger object, an icon or patch of color on a display monitor, a button, markings on an object, edges of colored patterns, and the like. Reference locations may be identified by visible or invisible light. They may be based on the locations of entire objects or subsets of objects, such as corners, voids, points, or edges. Light from reference locations may utilize ambient light, light projected from the eyewear or headwear, light generated by the reference locations themselves, and/or light from other sources. Combinations of both general approaches (i.e., recognizing both naturally occurring and intentionally placed objects) are also possible.

In light of the foregoing background, the apparatus, systems, and methods herein may provide an improved gaze tracking method and system for various applications.

In an exemplary embodiment, a method involves the use of a "scene camera" that is affixed to eyewear or headwear looking outwardly relative to the individual wearing the eyewear or headwear. The scene camera transmits images to a processor programmed to identify multiple reference locations within scene camera images. Optionally, the processor may be coupled to, may communicate with, or may otherwise access a database of "templates," (i.e., images of known objects, configurations of reference locations, and the like) to identify reference locations.

In accordance with one embodiment, systems and methods are provided that identify reference locations using image recognition techniques to identify objects or components of objects with known geometries and colors. A common configuration using this method is to identify the four corners of a computer display monitor or mobile computing/phone device or other electronic object. This may be performed by recognizing the edge of the device frame relative to a background scene, the edge of the display screen (i.e., the backlit region in the case of a LCD-based device or object) relative to the frame of the display, or both. Corners and/or edges may be identified based on color, texture, sharp versus rounded geometry, size relative to other identifiable components, markings, and the like.

In accordance with another embodiment, systems and methods are provided that produce reference locations in which identifiable objects or surfaces have been added to a scene at known locations. For example, systems and methods may use pieces of paper or plastic conveniently affixed to objects (e.g., using adhesive, screws, clips, or other fasteners, and the like) that may be identified based on color and/or shape. Similarly, ink, paint or other pigmented substances may be applied to objects to generate reference locations with an identifiable color or shape. The color and/or shape of the applied reference surface may be based on measuring reflected, fluorescent, phosphorescent, or luminescent light that may be either visible or invisible.

In accordance with yet another embodiment, systems and methods are provided that produce bright reference points using reflective patches (e.g., constructed from paint, cloth, plastic, paper, and the like) that may be affixed to any surface (e.g., using adhesive, fasteners, and the like). These reflective surfaces may be based on prismatic or flat reflective mirrored surfaces. They may be illuminated using one or more light sources located on the eyewear or headwear, by ambient light, and/or other light sources. One example of a light source is a single or multiple light-emitting diodes (LEDs) located adjacent to or away from the scene camera on the eyewear or headwear. The light sources may use wavelengths of electromagnetic radiation that are visible or invisible, e.g., infrared or other light outside the visible spectrum to avoid interference with normal activities of the wearer and/or others. In this configuration, the timing of illumination may be controlled by the eyewear or headwear and no illumination sources powered external to the eyewear or headwear may be required.

In accordance with still another embodiment, systems and methods are provided that not only provide bright reference locations illuminated by the eyewear or headwear, but also produce reference glints by the light reflected from the reference points onto the eyeball. By controlling the timing of illumination relative to the timing of video image acquisition, it is possible to acquire images with and without illumination of reflective reference points and glints. Subtracting images with illumination turned on, from images with illumination turned off, may facilitate the ability to isolate the locations of reflective sources including the locations of the reference points within images acquired by scene cameras as well as the locations of corresponding glints within images gathered by eye tracking camera(s).

A controller may be coupled to the camera(s) and/or the light sources that is configured for sampling brightness in the respective reflected reference locations of the light sources using the camera(s) and modulating the light source(s) based on the sampled brightness to provide desired brightness levels within camera images.

A processing unit operationally coupled to the scene camera may acquire images of the environment of the device wearer, for example, to monitor and/or further analyze characteristics of the scene. The scene processing unit and eye-tracking processing unit may be one or more separate processors, or may be a single processor and/or may include illumination controllers to regulate the intensity of illumination of the environment to the device wearer.

In one embodiment, the illumination controller may be configured for amplitude modulation of at least one of the current and/or the voltage to the light source to provide desired brightness levels in the respective regions of scene camera images. In addition or alternatively, the controller may be configured for pulse-width modulation of the current and/or the voltage to the light sources to provide desired brightness levels.

In any of these examples, illumination, reference location tracking, eye tracking and gaze tracking may be operated substantially continuously or intermittently. For example, scene light sources may be deactivated when the scene camera is inoperative. This includes times between acquiring camera images. Processors, cameras and illumination may also be deactivated when not in use, e.g., to conserve power. Illumination sources and other electronics may also be reduced in power or turned off for increased safety of the device wearer.

In an exemplary embodiment, the system includes an eyewear or headwear frame, a scene camera directed to view the environment around a device wearer, at least one camera directed at an eye of the wearer, one or more illumination sources oriented towards at least one eye of the wearer, and one or more processors, e.g., a scene processing unit coupled to the scene camera to identify reference locations within scene camera images, and a processing unit for eye tracking. The system may also include one or more light sources on the frame oriented away from the wearer, e.g., to provide scene illumination when reflective reference locations are utilized. Machine vision techniques are used within the processing unit(s) to determine reference locations. Reference locations identified within the scene processing unit and the eye-tracking processing unit may then be used in gaze tracking calculations.

Other aspects and features of the present invention will become more apparent from consideration of the following description taken in conjunction with the accompanying drawings

BRIEF DESCRIPTION OF THE DRAWINGS

The drawings illustrate exemplary embodiments of the invention, in which.

DETAILED DESCRIPTION OF THE EXEMPLARY EMBODIMENTS

Figure 1:
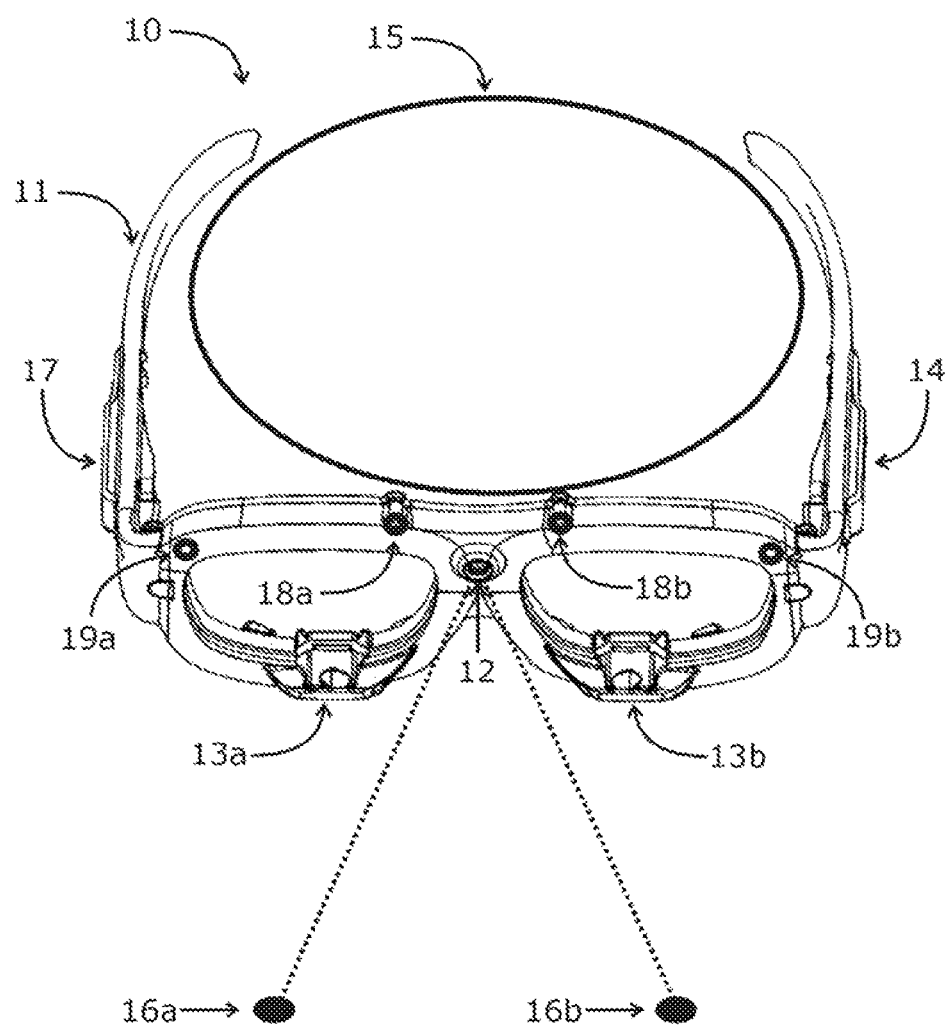
FIG. 1 is a perspective view of an example of a system mounted on eyeglasses frames for reference location tracking and eye tracking.

Turning to the drawings, FIG. 1 shows an exemplary embodiment of a system 10 including an eyeglass frame 11 with a scene camera 12, two eye-tracking cameras 13a, 13b, and a processing unit 14. Scene camera 12 is oriented on the frame 11 to view the region away from the device wearer's head 15 in order to track one or more reference locations 16a, 16b within the environment of the device wearer. Eye-tracking cameras 13a and 13b are oriented on the frame 11 toward the head 15 in order to track the locations of the wearer's pupils, glints, and/or other reference points on one or both eyes of the wearer.

In this embodiment, a single processing unit 14 may be carried by the frame 11, e.g., to acquire images from the scene camera 12 as well as the eye-tracking cameras 13a, 13b, although it will be appreciated that separate processors (not shown) may be provided on the frame 11 or at a remote location (not shown) that communicates with the frame 11. A power source (e.g., battery) 17 may be carried by the frame 11, e.g., encased in the stem of the frame 11 opposite that containing the processing unit 14. Scene illumination light sources 18a, 18b may optionally be located near the scene camera 12 or more distant from the scene camera 12.

Figure 6:
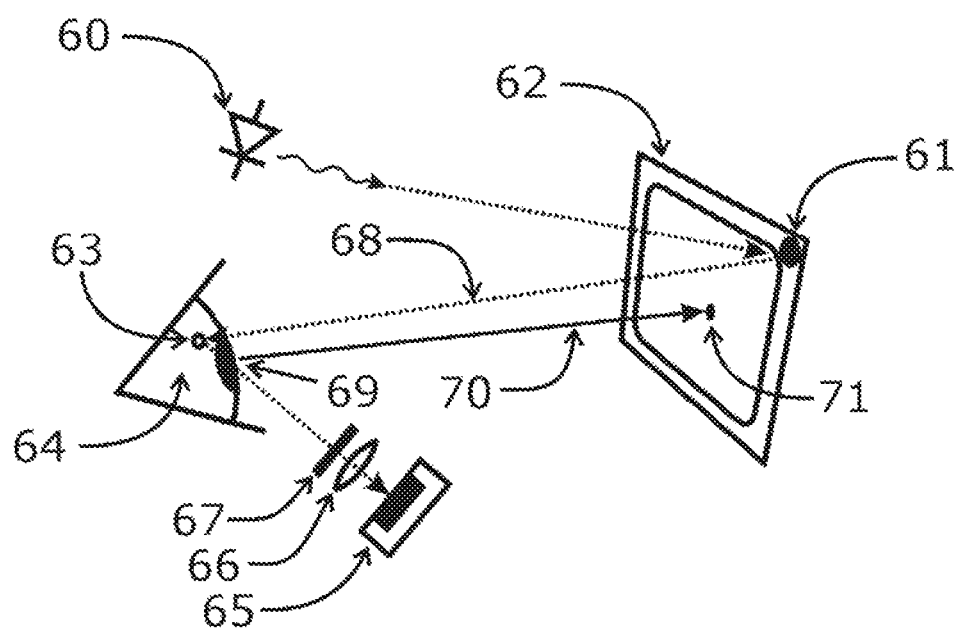
FIG. 6 is an example of an illumination pathway that shows a reflective surface that may be detected by a scene camera as a reference location, and a glint on the surface of the eye that may be detected by an eye-tracking camera.

In an exemplary embodiment, the scene camera 12 may include a CCD or CMOS or other detector including an active area, e.g., having a rectangular or other array of pixels, for capturing images and generating video signals representing the images. The active area of the camera 12 may have any desired shape, e.g., a square or rectangular shape, and the like. In addition, the camera 12 may include one or more filters, lenses, and the like (e.g., filter 67 and/or lens 66 as illustrated in FIG. 6), if desired, e.g., to focus images on the active area, filter undesired intensities and/or wavelengths of light, and the like.

In the embodiment illustrated in FIG. 1, the scene camera 12, is unobtrusively located on the nose bridge 25 (FIG. 2) of the frame 11, thereby minimizing interference with the wearer's normal vision. Other locations for the scene camera(s) are also possible including near the outer edges of the frame 11. Alternatively, in the case of headwear, one or more scene cameras may, for example, be located atop the head (not shown). Reflective and/or refractive optical components may be incorporated, e.g., to direct light from different regions of the environment towards scene camera(s).

In addition or alternatively, multiple scene cameras 19a, 19b may be provided that are spaced apart from one another and/or directed towards multiple reference locations 16a, 16b, e.g., providing separate or overlapping fields-of-view. Multiple scene cameras 16a, 16b may provide higher resolutions, increased sensitivity under different lighting conditions and/or a wider field-of-view, e.g., in addition to or instead of scene camera 12. Another potential advantage of using multiple scene cameras is the ability to use different optical filters (e.g., see filter 67 in FIG. 6) with each camera, e.g., to isolate reference sources that differ in color or that are preferentially illuminated using different wavelengths of electromagnetic radiation.

If two (2) scene cameras are used, they may, for example, be conveniently located near each of the outer corners of the frame 11 (e.g., near locations indicated as 19a and 19b in FIG. 1) or lateral sides of headgear (not shown). Reference locations and corresponding scene camera orientations may be within the normal visual field of the wearer or outside of this range including directed beside or behind the head. Field(s)-of-view may optionally be controlled in size and/or location by reflective surfaces and refractive lenses.

Figure 2:
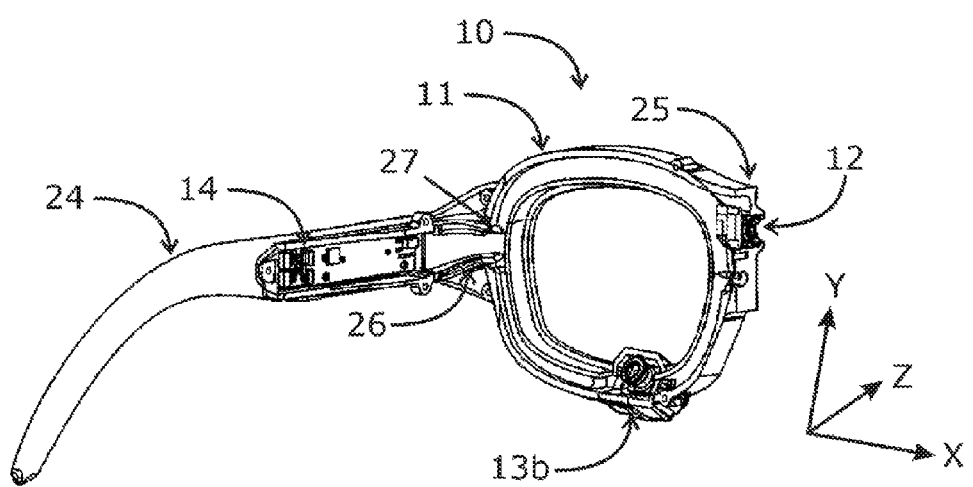
FIG. 2 is a partial cut-away, side view of the system of FIG. 1, showing the spatial relation between a scene camera and an eye-tracking camera; and connections among a processing unit, scene camera, eye-tracking camera, and other components.

FIG. 2 shows a cut-away view and back side of the system 10 illustrated in FIG. 1. The fixed spatial displacement between scene camera 12 and eye-tracking camera 13b mounted within eyeglasses frames 11 in X, Y and Z directions may be seen from this perspective. FIG. 2 also shows an example of a location where a single processing unit 14 for reference location tracking and eye-tracking may be embedded within the stem of the frame 11. In this exemplary embodiment, the processing unit 14 is a field-programmable gate array (FPGA).

The processing unit 14 may include one or more controllers or processors, e.g., one or more hardware components and/or software modules for operating various components of the system 10. For example, the processing unit 14 may include a separate (not shown) or integral controller for controlling light sources or cameras, for receiving and/or processing signals from cameras 12, 13b, and the like. Optionally, one or more of the components of processing unit 14 may be carried on ear supports 24, on the lens supports of the frame 11, nose bridge 25, and/or other locations within the eyewear or headwear, similar to embodiments described in the references incorporated by reference elsewhere herein. In the exemplary embodiment shown in FIGS. 1 and 2, a single processing unit 14 is used for image acquisition and processing for both reference location and eye tracking functions.

Cable(s) 26 may include individual cables or sets of wires coupled to cameras 12, 13b, battery 17 (FIG. 1), light sources 18a, 18b (FIG. 1) and/or other components on the frame 11 and/or to processing unit 14. For example, individual cables or sets of wires (not shown) may be embedded in the frame 11, e.g., along the rim from the cameras 12, 13b, and the like, until captured within the cable 26, e.g., to reduce the overall profile of the frame 11 and/or to direct signals around any hinged regions or corners 27 within the eyewear or headwear, as desired.

The processing unit 14 may also include memory (not shown) for storing image signals from the camera(s) 12, 13b, filters for editing and/or processing the image signals, elements for measurement calculations (also not shown), and the like. Optionally, the frame 11 and/or processing unit 14 may include one or more transmitters and/or receivers (not shown) for transmitting data, receiving instructions, and the like. In addition or alternatively, at least some processing may be performed by components that are remote from the frame 11 and/or on-board processing unit 14, similar to embodiments disclosed in the references incorporated by reference elsewhere herein. For example, a data acquisition system may include one or more receivers, processors, and/or displays (not shown) at one or more remote locations from the processing unit 14 and/or frame 11, e.g., in the same room, at a nearby monitoring station, or at a more distant locations. Such displays may include views generated by the scene camera(s) 12 and/or eye-tracking camera(s) 13b, as well as gaze tracking measurements and related calculations.

Figure 3:
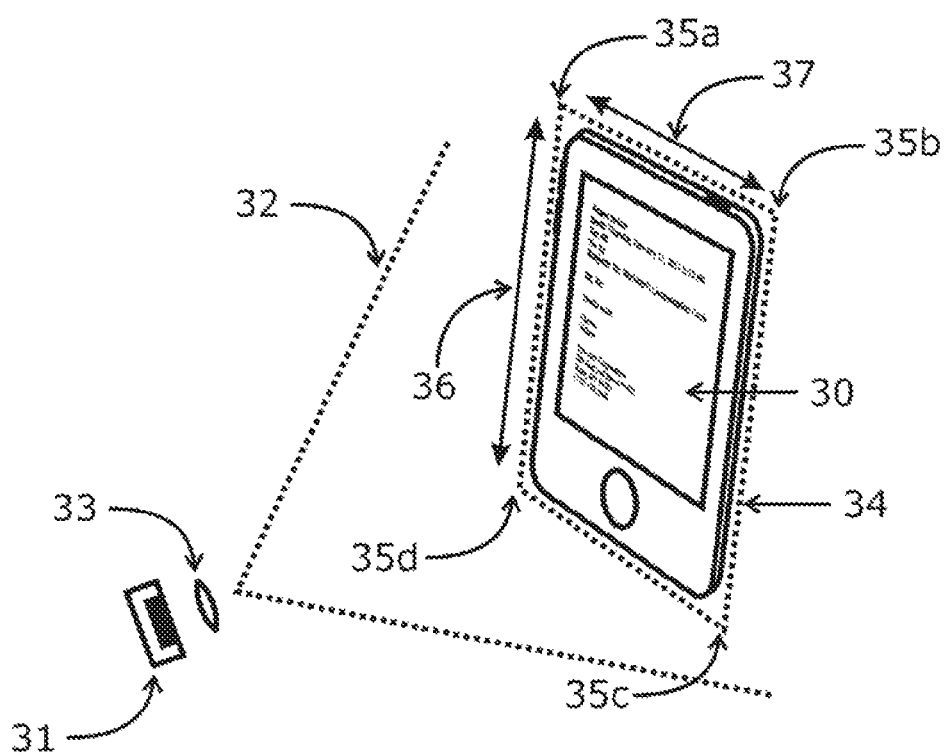
FIG. 3 shows an exemplary method for detecting reference locations using object recognition within an unaltered scene that includes a mobile computing/phone device.

FIG. 3 is an example of reference location tracking where machine vision techniques involving object identification are used to locate objects with known geometries and/or colors within an "unaltered scene" (i.e., a scene not altered intentionally for the purpose of establishing reference locations by the wearer/observer or anyone else involved in observations). In this example, the size, orientation, and/or location of a conventional mobile phone or hand-held computing device 30 may be tracked using a scene camera 31. Images may be brought into focus on a scene camera 31 (which may be similar to the scene camera 12 shown in FIGS. 1 and 2), e.g., using one or more lenses 33, which may be carried by or otherwise coupled to the scene camera(s) 31 (not shown).

Within images acquired by the scene camera 31, a processing unit (not shown) may scan the field-of-view 32 of images from the scene camera 31 for objects similar in shape and color to an object template for a mobile computing device. For example, the processing unit may include or otherwise access a database of known templates, e.g., a table associating known objects with data identifying their shapes and/or colors. The database may include vertical and horizontal reference points 36, 37 of known objects, detailed color and/or shape information on the reference objects, and the like, mapped to particular physical objects, thereby providing the processing unit sufficient information to identify the encountered object. If an object with appropriate attributes is found, a tetragon 34 (in this example of a rectangular cell phone) may be used to define the boundary of the device within images from the scene camera 31. The dimensions of the sides of the tetragon 34 may be used to compute the orientation of the location of the scene camera 31 relative to reference points within the mobile computing device 30. The overall size of the tetragon 34 within images from the scene camera 31 may be used in calculations of the distance between the scene camera 31 (i.e., affixed to the eyewear or headwear 11) and reference points within the mobile computing device 30.

Examples of reference locations within reference objects include the four (4) corners of the tetragon 34 that correspond to the four (4) corners 35a, 35b, 35c, 35d of the mobile computing device 30. The vertical 36 and horizontal 37 real-world dimensions of the reference object are known to the scene camera processing unit and, along with measurements made in scene camera images, may be used to translate distances measured within the images from scene camera 31 into real-world dimensions.

Figure 4:
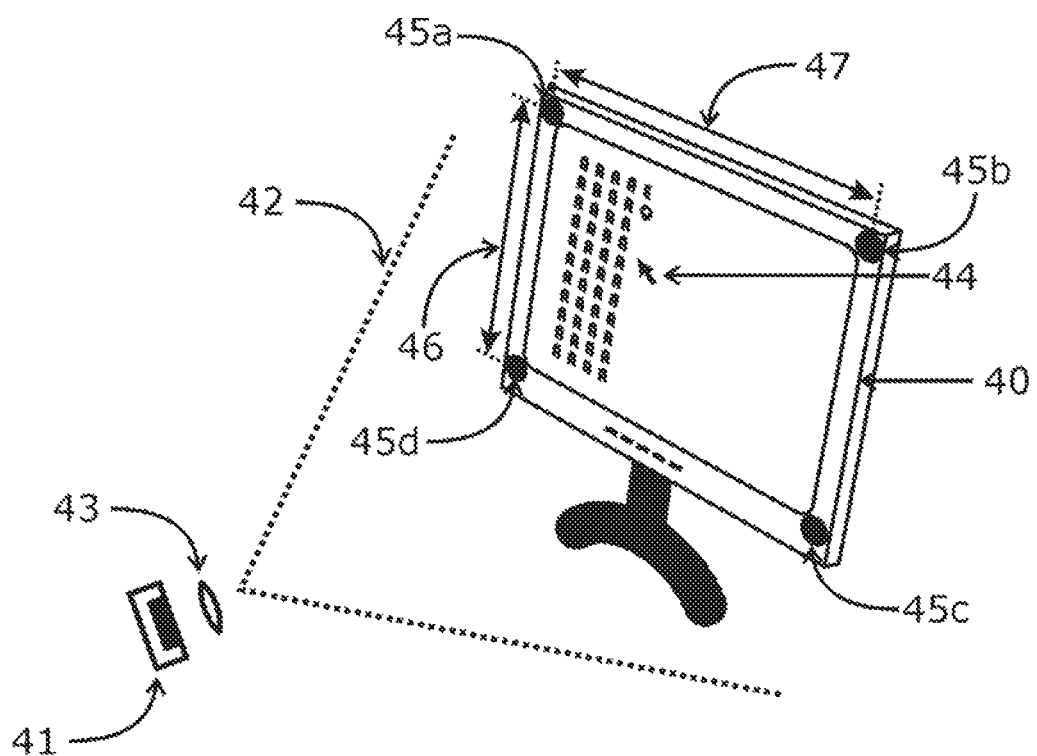
FIG. 4 shows another exemplary method for detecting reference locations that includes providing reference objects, e.g., four (4) identifiable, colored, round pieces of paper, on the four (4) corners of a display monitor.

FIG. 4 is an example of reference location tracking where reference objects have been intentionally placed within a wearer's environment. Machine vision techniques involving object identification are used to locate these objects with known geometries and/or colors within scene camera images. In this case, four (4) discs 45a, 45b, 45c, 45d of known size(s) and color(s) have been affixed to the four (4) corners of display monitor 40, e.g., by bonding with adhesive. Alternatively, the monitor 40 or other device may include reference objects permanently attached or otherwise incorporated into the device at desired locations.

Any number of reference objects may be added to the wearer's environment, e.g., two or three, or more than four (not shown), if desired. Reference objects may be of any size, shape or color. Reference objects may all be substantially the same size, shape and/or color; or one or more reference objects may differ in size, shape and/or color. In the latter example, differences in size, shape or color may be useful in unambiguously determining the exact orientation of reference locations and associated objects, e.g., to uniquely identify each corner of the mobile computing device 30.

With further reference to FIG. 4, images may be brought into focus on scene camera 41 (which may be similar to the scene camera 12), e.g., using a lens 43. Employing images acquired by the scene camera 41, a processing unit (not shown) may scan the field-of-view 42 of the scene camera 41 for objects similar in shape and/or color to an object identification template for intentionally placed reference objects, e.g., accessing a database of templates, as described elsewhere herein. When objects with appropriate attributes are found, the distances between the centers or edges of reference objects 45$a$, 45$b$, 45$c$, 45$d$ may be measured in vertical 46 and horizontal 47 directions. These distances may then be used to compute the orientation of the location of the scene camera 31 relative to reference points 45$a$, 45$b$, 45$c$, 45$d$ within the scene. The overall size of the tetragon defined by the four (4) corners of reference objects 45$a$, 45$b$, 45$c$, 45$d$ may also be used in calculations of the distance between the scene camera 41 and locations within the scene. Known real-world distances between vertical 46 and horizontal 47 reference points may be used to translate distances measured within the images from a scene camera 41 into real-world dimensions.

One application of head tracking and gaze tracking using these techniques is to control the position of a computer cursor 44 displayed on a monitor 40. The accurate control of a cursor using gaze tracking may result in a wide range of applications including using a computer to surf the Internet, control a game, generate text-to-speech, turn on/off lighting or other environmental controls in household or industrial settings, and so on. Tracking head and eye movements while an observer is instructed to closely follow an object such as a cursor 44 may also be used during calibration procedures that, for example, may be used to account for spatial aberrations within a field-of-view 42, such as those produced by most lenses 43.

Figure 5:
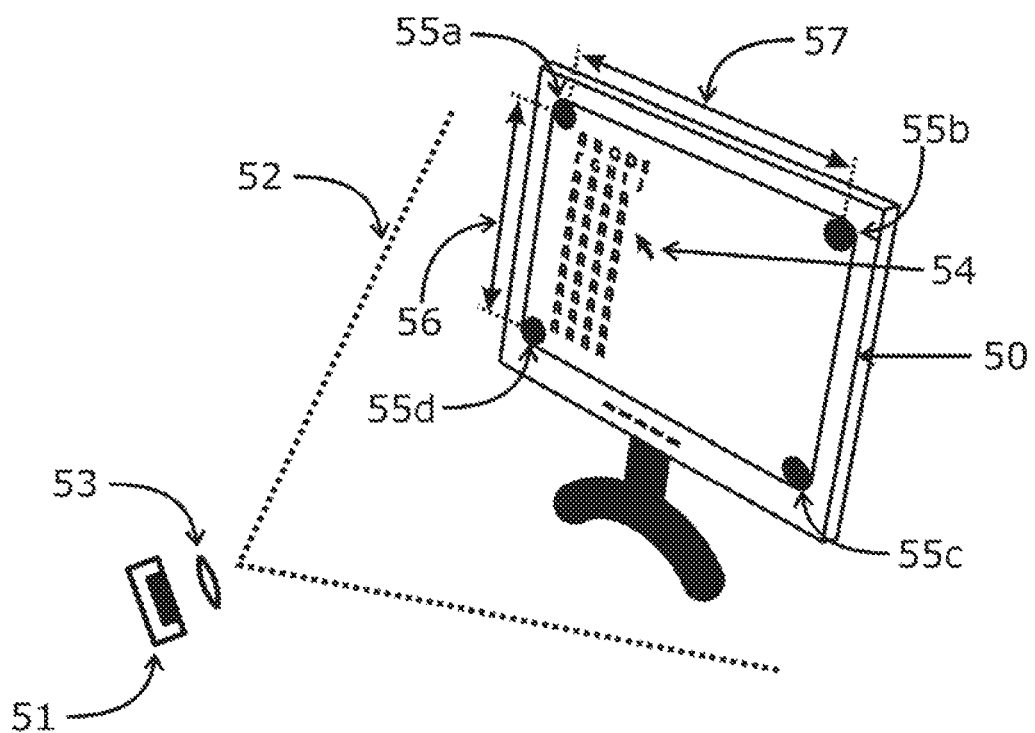
FIG. 5 shows yet another exemplary method for detecting reference locations that includes providing "virtual" identifiable reference objects, e.g., four (4) colored, regions displayed in the four (4) corners of a display monitor.

FIG. 5 shows another example of reference location tracking where "virtual" reference objects are intentionally displayed on a monitor or screen 50 that is within the field-of-view 52 of a scene camera 51. "Virtual" reference objects may, for example, be patches of color, icons, QR codes, and/or other visual patterns that are distinct from the screen's background. For example, the drivers for the monitor 50 may be modified or replaced such that the virtual objects are superimposed on any images otherwise displayed on the monitor 50. Thus, even when the monitor is used to display images and/or otherwise operate a variety of programs, the virtual objects may be present. The virtual objects may remain substantially static in the images presented on the monitor 50 or may moved during, e.g., as described elsewhere herein.

Machine vision techniques may be used to locate these "virtual" objects with known geometries, spatial relationships and/or colors within the scene. In the example illustrated in FIG. 5, four (4) "virtual" objects 55$a$, 55$b$, 55$c$, 55$d$ are displayed in the four (4) corners of a display monitor 50. Any number of "virtual" reference objects may be added to the field-of-view 52 of the scene camera 51. The "virtual" reference objects may be of any size, shape or color. The "virtual" reference objects may all have substantially the same size, shape, spatial distribution of geometric forms and/or color; or one or more "virtual" reference objects may differ in size, shape and/or color. In the latter example, differences in size, shape, spatial distribution of geometric forms and/or color may be useful in unambiguously determining the rotational orientation of reference locations, similar to other embodiments herein.

When virtual objects with appropriate attributes are found, e.g. by a processing unit analyzing the images from the scene camera 51, the distances between the centers of objects 55$a$, 55$b$, 55$c$, 55$d$ may be measured in vertical 56 and horizontal 57 directions. These distances may be used to compute the orientation of the location of the scene camera 51 relative to reference points 55$a$, 55$b$, 55$c$, 55$d$ within the environment of the device wearer. The overall size of a tetragon defined by reference objects 55$a$, 55$b$, 55$c$, 55$d$ in the four (4) corners of the display screen may be used in calculations of the distance between the scene camera 51 and locations within the scene. Known real-world distances between vertical 56 and horizontal 57 reference points may be used to translate distances measured within images from the scene camera 51 into real-world dimensions. For example, the processing unit may include or access a database of templates that includes sufficient information to identify the object actually encountered, similar to other embodiments herein. Head tracking and gaze tracking measurements using these techniques may be used, e.g., to control the position of a cursor 54 displayed on the computer monitor 50 and/or otherwise interact with the encountered object and/or other nearby objects.

An advantage of using "virtual" reference objects as depicted in FIG. 5 is the ability to generate identifiable reference objects without any (hardware) modifications of real-world objects. For example, if a computer (not shown) is to be used by a wearer of the system 10 of FIG. 1, software may be loaded onto the computer, e.g., modifying or replacing the monitor driver(s) and/or otherwise causing the virtual reference objects to be included in images displayed on the computer's monitor 50 during use of the system 10. Conversely, the use of physical reference object placed, for example, on the edge of a computer monitor 40 as depicted in FIG. 4 obviates the need for any superimposed display (and associated software modifications) within the displayable area of a monitor 40.

With further reference to FIGS. 4 and 5, it is possible to combine any number of real reference objects with any number of "virtual" reference objects within a scene. Machine vision techniques using images from one or more scene cameras may be used to track any number of such objects. For example, the tracking of physical objects may be used initially when viewing reference objects in certain orientations and directions to identify a screen or device being operated by or communicating with a system, such as system 10 of FIG. 1. Identification of "virtual" objects may then be used when appropriate screen viewing angles are present, e.g., after the physical objects have been used to identify the monitor or screen. In order to produce highly precise gaze tracking within a localized area on a screen, for example, it may be desirable to dynamically change the positions or other tracking characteristics of "virtual" reference objects, e.g., once gaze tracking has determined where on the monitor or screen the wearer is looking. For example, more closely spaced, smaller "virtual" reference objects may be use as attention is focused to a particular subset or area of a monitor or screen. A processing unit may then discard image data outside of the field of the virtual objects on the monitor or screen, e.g., to enhance accuracy in gaze tracking, reduce the size of image data stored and/or processed, and the like.

FIG. 6 shows an example of an illumination and optical pathway that takes advantage of reflective reference patches and associated locations. In this example, an illumination source (e.g., one or more LEDs) 60 is included within or otherwise carried by the eyewear or headwear (not shown, such as the frame 11 of FIGS. 1 and 2). Electromagnetic radiation from this illumination source 60 reflects off of one or more reflective patches or surfaces 61 that have been added to or embedded within one or more objects within the scene at known locations. In this exemplary embodiment, light is reflected from a disc 61 affixed to the corner of a display monitor or mobile computing device 62. The location of this reflective surface and other reference surfaces in the scene may be determined from images gathered using a scene camera (not shown in FIG. 6, see, e.g., scene camera 12 in FIGS. 1 and 2).

With additional reference to FIG. 6, light reflected from the reflective reference surfaces may produce glints 63 on the surface of the eye 64. Glints may be detected as high-intensity bright spots within images gathered using eye-tracking camera(s) 65. Within the eyewear or headwear, a short working distance lens 66 is generally required to focus images from eye 64 onto eye-tracking camera 65, and a filter 67 may optionally be included in the light pathway to isolate optical wavelengths produced by the reflective (fluorescent, phosphorescent or luminescent) reference location surfaces.

A line segment between the center of glint 63 and the center of the corresponding reference location 61 produces a vector 68 that may be used as an input to gaze tracking calculations. This reference vector 68 along with the location of the center of the pupil 69 may then be used to compute a gaze tracking vector 70 relative to the reference vector 68. Additional considerations in calculating a gaze tracking vector 70 include the slightly offset location of the center of the fovea (i.e., the image-sensing region of the retina) relative to the measured center of the pupil 69 and refraction within the light path through the cornea (not shown). The gaze tracking vector 70 points to the location 71 being viewed by the observer (i.e., the wearer of the eyewear or headwear).

Returning to FIGS. 1 and 6, an advantage of having illumination source(s) on the eyewear or headwear, e.g., frame 11, is the ability to conveniently control the timing and/or intensity of illumination compared to the acquisition of images by scene camera 12 and eye-tracking 13a, 13b cameras. By subtracting scene images and/or eye-tracking camera images with illumination turned on from images with illumination turned off, reflections from reference locations 16a, 16b may be more readily isolated in scene camera images, and reflections from glints 63 may be more readily isolated in eye-tracking camera images. Furthermore, this scheme obviates the need for any light source or other powered component to be located away from, or tethered to, a power source 17 or controller within the eyewear or headwear. Thus, if reference objects are attached to or incorporated into a monitor or screen of a device, such reference objects do not need to be provided with a power source and/or controller to generate light, but may merely reflect light from the illumination source(s) 60.

Any number of reflective surfaces 61 may be used as reference locations and/or sources for the production of glints 63. Any number of sources of electromagnetic radiation may generate visible or invisible light. Using invisible light to produce reflections at reference locations and glints on the eye is particularly convenient, as this scheme generates little or no distraction (due to the presence of potentially bright, reflected light) on the part of a device wearer. CMOS cameras, in particular, are capable of detecting electromagnetic radiation in the near infrared spectrum that is not visible to the human eye. CMOS cameras are also particularly well suited in applications where low power and/or miniaturization are desired.

As described further elsewhere herein and with reference to FIG. 6, the brightness levels of glints 63 measured using an eye-tracking camera 65 and reflections from reference locations 61 measured using scene camera(s) 12 (not shown, see FIG. 1) may be used in a feedback mode to control the intensity of the illumination source(s) 60. One or more illumination sources 60 may be used to illuminate reference locations, for example, multiple illumination sources 60 (not shown) mounted at multiple locations throughout the eyewear or headwear. The use of multiple illumination sources 60 illuminating the environment of the device wearer from different angles may help to maintain high intensity reflections in camera images at different viewing angles.

In one embodiment, the amplitude of either the voltage or the current driving each illumination source 60 may be used to control light intensity. This is generally referred to as "amplitude modulation." In another embodiment, the duration or "dwell time" of a controlling voltage or current may be modified to control light intensity. This is generally referred to as "pulse-width modulation." Optionally, it is also possible to use both schemes simultaneously.

In an exemplary embodiment, each illumination source 60 may include a LED (light emitting diode) configured for emitting a relatively narrow or wide bandwidth of light, e.g., near infrared light at one or more wavelengths between about 640-700 nanometers, broadband visible light, white light, and the like. Optionally, one or more of the illumination sources 60 may include lenses, filters, diffusers, reflectors, or other features (not shown), e.g., for facilitating and/or controlling the uniformity of lighting of the environment of the device wearer. The illumination source(s) 60 may be operated substantially continuously, periodically, or otherwise intermittently, e.g., such that desired scene images are illuminated by the source(s) 60, and then the images may be processed using the systems and methods described elsewhere herein.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented methods and/or processes as a particular sequence of steps. However, to the extent that the methods or processes do not rely on the particular order of steps set forth herein, the methods or processes should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed is:

1. A system for determining reference locations, comprising:
   a device configured to be worn on a wearer's head;
   a scene camera mounted on the device oriented away from the wearer for capturing scene camera images of the environment of the wearer;
   an eye-tracking camera mounted on the device oriented towards an eye of the wearer for capturing eye-tracking locations of at least one of the wearer's eyes;

a database of templates mapping known objects with scene reference locations associated with respective known objects; and one or more processors coupled to the scene camera for determining scene reference locations within the scene camera images and coupled to the eye-tracking camera, the one or more processors using the scene reference locations and the eye-tracking locations to determine locations being viewed by the wearer, the one or more processors communicating with the database for identifying an object associated with the scene reference locations acquired from the scene camera images, and wherein object recognition algorithms are used by the one or more processors to identify the scene reference locations within the scene camera images.

2. The system of claim 1, wherein object recognition is based at least in part on a shape of an object, a color of an object, and at least one edge of an object.

3. The system of claim 1, wherein the one or more processors use object recognition to identify a location of at least one of the corners of a display device.

4. The system of claim 1, further comprising reference objects affixed to the object within a field of view of the scene camera, the object located within the scene camera images such that the reference objects are recognized by the one or more processors.

5. The system of claim 1, further comprising one or more light sources on the device and oriented away from the wearer to illuminate the environment of the wearer.

6. The system of claim 5, wherein the one or more processors comprise a controller coupled to the one or more light sources for modulating the one or more light sources to desired brightness levels.

7. The system of claim 5, wherein the scene reference locations comprise one or more reflective reference objects on the object, and wherein the one or more processors comprise a controller coupled to the one or more light sources for operating the one or more light sources intermittently such that the reference objects are alternately illuminated and unilluminated in the scene camera images, the one or more processors configured for subtracting illuminated images including the reference objects from corresponding unilluminated images including the reference objects acquired by the scene camera images to enhance identification of the reference objects.

8. A method for determining reference locations, comprising:
    placing a device on a wearer's head;
    providing a scene camera on the device positioned for capturing images of the environment of the wearer, the scene camera coupled to a scene processor for determining scene reference locations within scene camera images acquired from the scene camera; and
    providing an eye-tracking camera on the device positioned for capturing eye-tracking locations of at least one of the wearer's eyes, the eye-tracking camera and the scene camera coupled to a processor for using the scene reference locations and the eye-tracking locations to determine locations being viewed by the wearer,
    wherein the processor is coupled to the scene camera for determining scene reference locations within the scene camera images and coupled to the eye-tracking camera, the processor using the scene reference locations and the eye-tracking locations to determine locations being viewed by the wearer, the processor communicating with a database of templates mapping known objects with scene reference locations associated with respective known objects for identifying an object associated with the scene reference locations acquired from the scene camera images, and wherein object recognition algorithms are used by the processor to identify scene reference locations within the scene camera images.

9. The method of claim 8, further comprising utilizing one or more light sources to illuminate the environment of the wearer.

10. The method of claim 9, further comprising positioning additional reflective objects within the environment of the wearer such that the additional reflective objects are recognized within the scene camera images.

11. The method of claim 8, wherein the object recognition is based at least in part on a shape of the object, a color of the object, and at least one edge of the object.

12. The method of claim 8, wherein the object is a display device, and wherein the scene reference location identified by the object recognition comprises a location of at least one corner of the display device to thereby identify the display device.

13. The method of claim 8, wherein the object is a display of an electronic device.

14. A method for determining reference locations, comprising:
    providing a device on a wearer's head, the device comprising a scene camera positioned for capturing images of the environment of the wearer, and an eye-tracking camera positioned for capturing eye-tracking locations of at least one of the wearer's eyes, the eye-tracking camera and the scene camera coupled to a processor for using the scene reference locations and the eye-tracking locations to determine locations being viewed by the wearer, the processor performing the method of:
    acquiring scene camera images of the environment around the wearer with the scene camera;
    identifying scene reference locations within the scene camera images to identify a physical object within the environment including a display;
    identifying one or more virtual reference objects on the display; and
    analyzing the eye-tracking images to determine locations being viewed by the wearer relative to the display based at least in part on the one or more virtual reference objects.

15. The method of claim 14, wherein the physical object is identified using object recognition.

16. The method of claim 15, wherein the object recognition is based at least in part on a shape of the physical object, a color of the physical object, and at least one edge of the physical object.

17. The method of claim 14, wherein the processor communicates with a database of templates mapping known objects with scene reference locations associated with respective known objects for identifying an object to identify the physical object.

18. The method of claim 14, further comprising changing one or more tracking characteristics of the one or more virtual reference objects on the display, and wherein analyzing the eye-tracking images further comprises analyzing, by the processor, the changing tracking characteristics to enhance gaze tracking within a localized area on the screen.

19. The method of claim 18, wherein changing one or more tracking characteristics comprises changing positions of the virtual reference objects on the display to define a field related to a particular subset or area of the display, and wherein the processor discards image data outside of the field to enhance accuracy in gaze tracking or reduce the size of image data processed by the processor.

\* \* \* \* \*